(12) United States Patent
Melotto et al.

(10) Patent No.: US 9,085,532 B2
(45) Date of Patent: Jul. 21, 2015

(54) PROCESS FOR PREPARING A KETOSULFONE DERIVATIVE

(71) Applicant: ZACH SYSTEM S.P.A., Bresso (IT)

(72) Inventors: Elisa Melotto, Lonigo (IT); Ivan Michieletto, Venice (IT); Vincenzo Frega, Vicenza (IT); Livius Cotarca, Cervignano del Friuli (IT); Massimo Verzini, Caldiero (IT); Franco Massaccesi, Grancona (IT); Ilaria Munari, Vicenza (IT)

(73) Assignee: ZACH SYSTEM S.P.A., Bresso (IT)

( * ) Notice: Subject to any disclaimer, the term of this patent is extended or adjusted under 35 U.S.C. 154(b) by 0 days.

(21) Appl. No.: 14/382,458

(22) PCT Filed: Mar. 8, 2013

(86) PCT No.: PCT/EP2013/054763
§ 371 (c)(1),
(2) Date: Sep. 2, 2014

(87) PCT Pub. No.: WO2013/135587
PCT Pub. Date: Sep. 19, 2013

(65) Prior Publication Data
US 2015/0133671 A1     May 14, 2015

(30) Foreign Application Priority Data

Mar. 14, 2012  (IT) .............................. MI2012A0394

(51) Int. Cl.
C07D 211/70    (2006.01)
C07D 213/50    (2006.01)

(52) U.S. Cl.
CPC .................................. *C07D 213/50* (2013.01)

(58) Field of Classification Search
None
See application file for complete search history.

(56) References Cited

U.S. PATENT DOCUMENTS 6,812,346 B2 * 11/2004 Dube et al. .................... 546/257

FOREIGN PATENT DOCUMENTS

WO         WO01/29003         4/2001

OTHER PUBLICATIONS

Grasa, et al., "A Highly Practical and General Route for alpha-Arylations of Ketones Using Bis-Phosphinoferrocene-Based Palladium Catalysts", Organic Process Research & Development 2008, 12, 522-529.
Written Opinion of the International Searching Authority for PCT/EP2013/054763, Mar. 21, 2013.

* cited by examiner

*Primary Examiner* — Heidi Reese
(74) *Attorney, Agent, or Firm* — Silvia Salvadori, P.C.

(57) ABSTRACT

The present invention relates to a process for preparing a ketosulfone derivative and, more particularly, to an improved method for synthesizing 1-(6-methylpyridin-3-yl)-2-[(4-methylsulfonyl)-phenyl]ethanone by means of Pd-catalized alpha arylation process of a heteroaromatic ketone derivative.

15 Claims, No Drawings

PROCESS FOR PREPARING A KETOSULFONE DERIVATIVE

This application is a U.S. national stage of PCT/EP2013/054763 filed on Mar. 8, 2013 which claims priority to and the benefit of Italian Application No. MI2012A000394 filed on Mar. 14, 2012, the contents of which are incorporated herein by reference in their entirety.

The present invention relates to a process for preparing a ketosulfone derivative and, more particularly, to an improved method for synthesising 1-(6-methylpyridin-3-yl)-2-[(4-methylsulfonyl)-phenyl]-ethanone by means of Pd-catalysed alpha arylation process of a heteroaromatic ketone derivative.

Ketosulfone derivatives are important molecules having several applications as synthons in processes for preparing pharmaceutical active ingredients.

More particularly the compound 1-(6-methylpyridin-3-yl)-2-[(4-methylsulfonyl)-phenyl]-ethanone has proven to be a key intermediate in the preparation of inhibitors of the cyclooxygenase-2 (Cox-2) enzyme, inter alias, the known etoricoxib.

Etoricoxib is a selective inhibitor of Cox-2 and has been found to be an effective anti-inflammatory non-steroidal non-selective drug in the treatment of chronic pain, rheumatoid arthritis, osteoarthritis and other Cox-2-mediated diseases.

Literature reports several processes for the preparation of etoricoxib and/or derivatives thereof.

U.S. Pat. No. 5,861,419 (Merck Frosst Canada, Inc.) describes a method for preparing Cox-2 inhibitors that comprises bromination of a 2-aminopyridine derivative, the coupling of the bromine derivative thus obtained with 4-(methylthio)-phenylboronic acid in the presence of a base and subsequent oxidation to give the corresponding sulfone; the amine group of the sulfone is converted into halide, which is subjected to a second Pd-catalysed coupling reaction with a suitable aromatic substrate to give the desired compounds according to the schema illustrated below

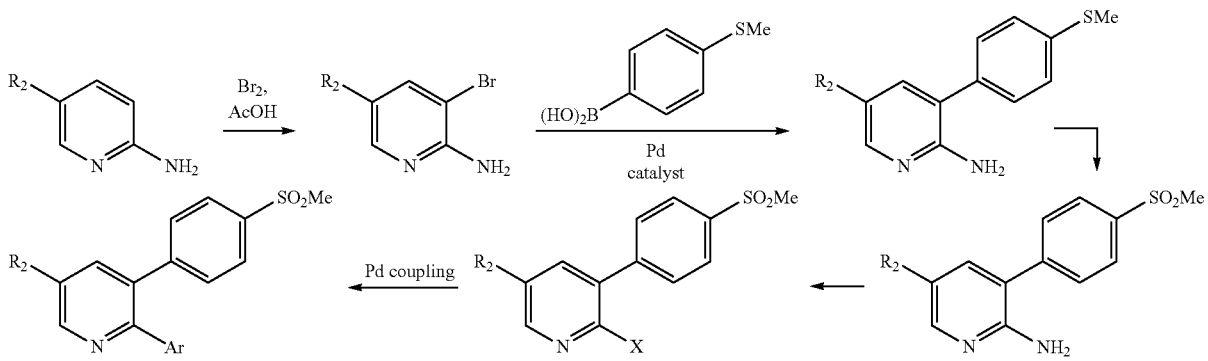

Similarly, U.S. Pat. No. 6,812,346 (Merck Frosst Canada, Inc.) describes a method for preparing etoricoxib that comprises reacting a compound of formula B, in which X is Br or Cl, with a compound of formula C, in which M is B(OH)$_2$ or SnMe$_3$, in the presence of a Pd-based catalyst to give the desired product according to the schema illustrated below:

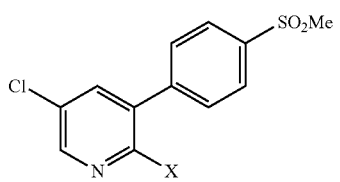

Formula B

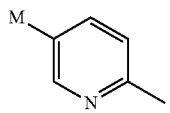

Formula C

The synthetic approach via ketosulfone derivative is reported in U.S. Pat. No. 6,040,319 (Merck & Co., Inc.), which describes a process for preparing Cox-2 inhibitors that comprises reacting the compounds of formulas II and III in the presence of a base according to the schema illustrated below:

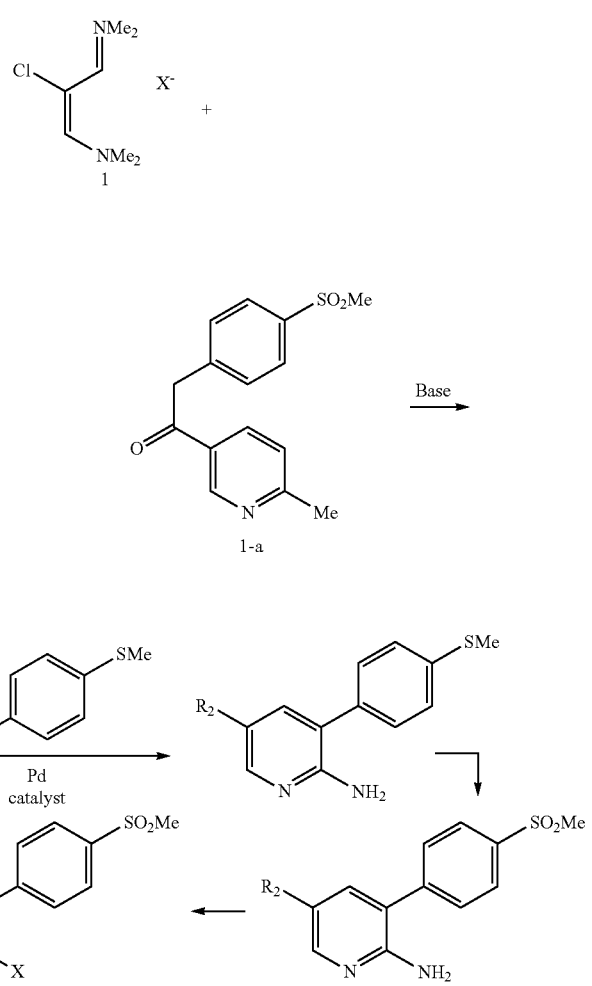

-continued

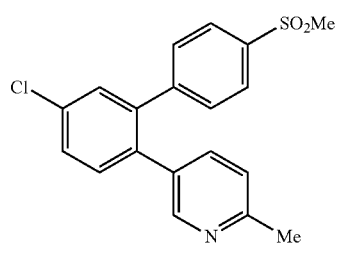

In particular, preparative Example 1 describes the multi-step synthesis of the compound 1-(6-methylpyridin-3-yl)-2-[(4-methylsulfonyl)-phenyl]-ethanone by preparation of a Weinreb amide from methyl 6-methylnicotinate and N,O-dimethylhydroxylamine, the conversion of said amide into the corresponding 4-thiomethylbenzyl ketone and subsequent oxidation to give the desired compound.

However, the reagents used suffer from several drawbacks from a synthetic point of view. Grignard reagent has to be prepared in situ from the corresponding 4-methylthiobenzyl halide; and the amide it self has to be prepared in THF in an anhydrous environment at a temperature of −10° C.

EP 1198455 (Lonza AG) describes a process for preparing 1-(6-methylpyridin-3-yl)-2-[(4-methylsulfonyl)-phenyl]-ethanone, characterised by five synthetic steps: chlorination of 4-(methylthio)-benzyl alcohol into the corresponding benzyl chloride; cyanidation of said chloride to give 4-(methylthio)-phenyl acetonitrile, which is condensed with a 6-methyl nicotinic ester to give 3-[2-[4-(methylthio)-phenyl)-2-cyanoacetyl]-(6-methyl)-pyridine; said pyridine derivative being then hydrolysed, decarboxylated and S-oxidised to give the desired product.

In addition, international patent application WO 2001/029003 (Zambon Group S.p.A.) describes a similar process for preparing intermediates useful in the synthesis of diarylpyridine having Cox-2-inhibitor activity.

However, both the above-mentioned synthetic methods suffer from several drawbacks in terms of the industrial application of the process.

In particular, the process described in EP' 455 consists of 5 synthetic steps with an overall yield around 38%; in the second step the keto-cyano derivative is carried out by using sodium or potassium cyanide, these being toxic gases of which the use requires special authorisation and technical equipment as well as trained personnel.

The process described in international application WO' 003 is based on a more advanced intermediate methylmercaptobenzonitrile and involves 3 synthetic steps and one purification step. The isolation of the intermediates and of the end product is complex with average yields of 65-75%.

Therefore, since the essential role of the compound 1-(6-methylpyridin-3-yl)-2-[(4-methylsulfonyl)-phenyl]-ethanone as key intermediate in the synthesis of diarylpyridine having Cox-2 inhibitor activity is known in the art, it would be desirable to study alternative methods allowing said intermediate to be prepared with good yields and under conditions more favourable in terms of the industrial application of the process.

We have now surprisingly found an improved process for synthesizing 1-(6-methylpyridin-3-yl)-2-[(4-methylsulfonyl)-phenyl]-ethanone, a key intermediate in the preparation of, inter alia, etoricoxib which allows to overcome the above-mentioned drawbacks of the described prior art processes.

Therefore, it is a first object of the present invention a process for preparing a compound of formula

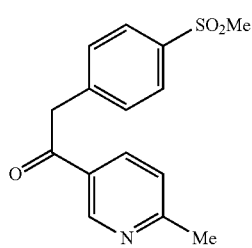

(I)

and salts thereof; which comprises the reaction of a compound of formula

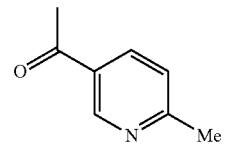

(II)

with a compound of formula

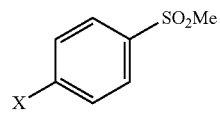

(III)

wherein X is halogen atom; in the presence of a catalyst, a ligand and a base; wherein said catalyst is a Pd catalyst complex and said ligand is an organophosphoric compound of formula 4,5-bis-(diphenylphosphino)-9,9-dimethylxanthene.

The compounds of formulas II and III, known in the prior art, are commercially available and/or can be prepared by common synthetic techniques.

For example, the compound of formula II can be prepared by the procedure reported in the open literature (J. Med. Chem. 1996, 39, 5053-5063); the literature also describes the oxidation reaction from sulphur to sulfone of formula III in Bull. Chem. Soc. Jpn. 1991, 64, 3752-3754.

The organophosphorus ligand of formula 4,5-bis-(diphenylphosphino)-9,9-dimethylxanthene is a commercially available compound commonly identified as Xantphos.

The reaction of a compound of formula II with a compound of formula III to give a compound of formula I and/or salts thereof is carried out in the presence of a catalyst, a ligand and a base by the technique of arylation of heteroaromatic ketones.

Salts according to the present invention are salts of mineral acids; the compound of formula I is preferably obtained from the reaction according to the invention in the form of hydrochloride salt.

The catalyst according to the invention is a Pd-based catalytic complex.

Preferred catalytic complexes are $PdCl_2$, $Pd(OAc)_2$, $Pd(dba)_2$ and $Pd_2(dba)_3$.

More preferred catalytic complex are $Pd(dba)_2$ and $Pd_2(dba)_3$.

The use of $Pd_2(dba)_3$, that is to say the Pd-based organometallic complex known as tris-(dibenzylideneacetone)-dipalladium(0) is still more preferred.

The catalytic complex is preferably used in a molar ratio to the substrate comprised between 0.01 and 2%; still more preferably around 0.05-0.10%.

In a preferred aspect of the invention, the loading of said preferred $Pd_2(dba)_3$ is between 0.05 and 0.5% and is preferably equal to 0.1 mol %.

The ligand suitable for the coupling reaction of the compounds of formulas II and III is the compound 4,5-bis-(diphenylphosphino)-9,9-dimethyl-xanthene.

The ligand is preferably used in a molar ratio to the catalytic complex comprised between 1.0 and 3.0; still more preferably between 1.5 and 2.5.

It is clear to a person skilled in the art that, in the reaction according to the present invention, it is possible to use pre-formed catalysts and catalysts where the complex-ligand coordination occurs within the scope of said reaction.

Bases suitable for the reaction according to the present invention are, for example, alkaline hydroxides or alkaline alkoxides.

The reaction is usually carried out in the presence of alkaline alkoxides, with sodium tert-butoxide being preferred In one aspect of the invention, said base is added to the reaction mixture in a single portion or intermittently as a suspension over about 6 hours; the addition is preferably made as a suspension over a period comprised between about 2 and 4 hours.

The base is preferably used in a molar ratio to the substrate comprised between 1.0 and 3.0, still more preferably between 1.5 and 2.5.

Generally, the reaction according to the invention is carried out in organic solvents.

Solvents suitable for the coupling reaction of the compounds of formulas II and III are polar and apolar aprotic solvents, such as ethers, hydrocarbons and, in particular, acetonitrile, diethoxyethane, 2,2-dimethoxypropane, 1,2-dimethoxyethane, dioxane, THF and toluene.

In such a case, the substrate is used in a concentration comprised between 0.05 and 0.40 M; preferably at a concentration comprised between 0.10 and 0.20 M.

The reaction is preferably carried out with alkaline alkoxides in the presence of aromatic hydrocarbons.

In accordance with a preferred aspect of the invention, the reaction is carried out with a base, such as sodium t-butoxide in the presence of toluene.

In the present invention, the term "halogen" means a fluorine, chlorine, bromine and iodine atom.

X is preferably a bromine atom.

The reaction according to the invention is generally carried out at a temperature comprised between 60 and 120° C. and the reaction is typically carried out at reflux temperature.

In accordance with a preferred aspect of the invention, the compounds of formulas II and III, the catalytic complex and the ligand are dissolved in an aromatic hydrocarbon, preferably toluene, and the solution thus obtained is brought to reflux and added by the base, preferably in solution or suspension; the reaction mixture is worked up and the product is precipitated as a free base or as an addition salt, preferably hydrochloride salt, which allows to isolate the compound with greater degree of purity.

The reaction of a compound of formula II with a compound of formula III according to the invention can be generically identified as Pd-catalysed alpha-arylation of a heteroaromatic ketone derivative with aryl halide Said method consists in the Pd-catalysed synthesis of an alpha-aryl carbonyl compound by reaction of an aryl electrophile, in the present case a halo-(methylsulfonyl)-benzene, with a stabilised enolated carbanion of 3-acetyl-6-methyl pyridine in an alkaline environment.

Generic α-arylation of aromatic ketones, in particular heteroaromatic ketones, are known in the art and are the subject of recent publications in the literature.

In particular, Mark R. Biscoe et al. (Org. Lett. 2009, Vol. 11, No. 8, p. 1773-5) describe simple, efficient procedures for mono-arylation of acetic esters and aryl methyl ketones by using aryl chlorides.

Changsheng Cao et al. (Eur. J. Org. Chem. 2011, p. 1570-4) describe a-arylation of ketones with aryl halides catalysed by Pd-based catalytic complexes.

Gabriela A. Grasa et al. (Org. Process R&D 2008, 12, 522-529) describe a generic method of α-arylation of ketones by using Pd-based catalysts of bis phosphine ferrocene.

To the best of the inventors knowledge, the Pd-catalysed alpha-arylation method according to the invention has never been described or suggested in the prior art.

In particular, the application of said method to the substrates according to the present invention or the use of the specific catalyst/ligand combination in the reaction according to claim 1 is neither known in the art nor suggested by any prior art reference.

It is important to underline that the person skilled in the art confronted with the preparation of Cox-2 inhibitors will surely be directed to conventional multi-step methods, where synthetic approach via ketosolfone derivatives has already been implemented by the prior art.

Therefore, we believe that the industrial development of an α-arylation method applied to the specific substrate according to the present invention is not obvious.

Therefore, the process according to the invention is aimed to simplify the preparation of a ketosulfone derivative by the use of substrates that are easily available on the market, moving from multi-step synthesis methods known in the art including four steps of isolation of intermediate products to a process having a single step that leads directly to the desired product.

It should also be borne in mind that the loading of the catalytic complex according to the invention is much lower compared to the loading of the generic α-arylation processes reported in the art, therefore, allowing to avoid purification steps, which are often complex and costly and are aimed at eliminating catalyst residues from the finished product and, not least, to minimise the effect of the cost of the catalyst on the economic viability of the process.

However, mono-arylation is selectively achieved thanks to the specific catalyst/ligand combination and the optimised stoichiometric ratio thereof; the bi-addition product is known to be the main impurity observed in the processes of alpha-arylation of methyl ketones reported in the art.

In addition, high yields (about 76%) and nearly total recovery of the catalyst and of the solvent from the reaction mixture complete the picture with a further advantage in terms of the economic viability of the process.

Of course, this implies a considerable reduction of production cost and obtainment of product having a purity such that it can be directly subjected to the subsequent stage of the process for preparing Cox-2 inhibitors.

Therefore, it is a further object of the present invention a process for synthesising etoricoxib that comprises the step of reacting a compound of formula II with a compound of formula III to give the compound of formula I, 1-(6-methylpyridin-3-yl)-2-[(4-methylsulfonyl)-phenyl]-ethanone, as reported above.

Therefore, it is readily apparent how the preparation method according to the invention constitutes an efficient and economical synthetic alternative in the preparation of key intermediates in the preparation of pharmaceutical active ingredients; in addition, the easy availability of the row materials used combined with the reduced number of synthetic steps and the good yields recorded, certainly, result in advantages that are not insignificant in terms of the costs and efficiency of the process.

A practical embodiment of the process according to the present invention, comprises charging in a reactor catalyst, ligand and substrates in toluene, preferably anhydrous toluene; the solution thus obtained is heated to reflux and a suspension of base in toluene is added over about 2 hours; at addition completed, the reaction mixture is kept at temperature for about 30 minutes and is, then, cooled to room temperature and is neutralised in an acidic solution; the phases are separated and the product can directly precipitate as addition salt or is precipitated and isolated as free base by adding the acidic solution to a suspension of ethyl acetate and sodium carbonate having a pH value comprised between 4 and 7.

To better illustrate the invention the following examples are now given.

EXAMPLE 1

Synthesis of 1-(6-methylpyridin-3-yl)-2-[(4-methylsulfonyl)-phenyl]-ethanone

Xantphos 0.027 g (0.0477 mmol) and Pd$_2$(dba)$_3$ 0.0182 g (0.0198 mmol) in 100 ml of anhydrous toluene were charged in a reactor under inert atmosphere. 4-bromophenyl methyl sulfone 9.3 g (39.7 mmol) and 3-acetyl-6-methyl pyridine 5.4 g (39.7 mmol) were then added. The mixture was heated to reflux and a suspension of t-BuONa 8.4 g in 100 ml of anhydrous toluene was added dropwise over about 4 h. After about 1 h from completion of the addition, the reaction mixture was cooled to 20° C. and a solution of diluted hydrochloric acid to acidic pH was added. The aqueous phase was separated and added dropwise over 1 h to a mixture of water 83.3 g, ethyl acetate 153 g and sodium bicarbonate 20.1 g at 60° C. At addition completed and after maintaining the temperature at 60° C. for 1 h, it was checked that the pH was between 4 and 7, the mixture was cooled to 20° C., filtered, and dried under vacuum at 50° C. 8.3 g of the compound of formula 1 were obtained with a yield of 72%.

EXAMPLE 2

Synthesis of 1-(6-methylpyridin-3-yl)-2-[(4-methylsulfonyl)-phenyl-ethanone hydrochloride 4-bromophenyl methyl sulfone 80.04 g (0.34 mol) and 3-acetyl-6-methyl pyridine 46.03 g (0.34 mol) in 800 ml of toluene were charged in a reactor under inert atmosphere. The mixture was heated to reflux and Xantphos 0.236 g (0.41 mmol) and Pd$_2$(dba)$_3$ 0.156 g (0.17 mmol) were added. A suspension of t-BuONa 72.08 g (0.75 mol) in 800 ml of toluene, kept at 60° C., was added dropwise over about 2 h. From the end of the addition, the reaction was kept for at least 1 h under stirring at that temperature before proceeding with the acid neutralisation. The mixture was cooled to 25° C. and a solution containing 25% hydrochloric acid was added. The mixture was heated to reflux and was distilled to obtain the crystallisation of compound I as hydrochloride. The product was isolated at 5° C. by filtration and was dried under vacuum at 50° C. with a yield of 70%.

EXAMPLE 3

Synthesis of 1-(6-methylpyridin-3-yl)-2-[(4-methylsulfonyl)phenyl]ethanone

Xantphos 0.00267 g (0.0046 mmol) and Pd$_2$(dba)$_3$ 0.00177 g (0.0031 mmol) in 15 ml of anhydrous toluene were charged in a reactor under inert atmosphere. 4-bromophenyl methyl sulfone 0.724 g (3.078 mmol) and 3-acetyl-6-methyl pyridine 0.416 g (3.079 mmol) were then added. The mixture was heated to reflux and a suspension of t-BuONa 0.71 g in 15 ml of anhydrous toluene was added dropwise over about 4 h. After about 1 h from completion of the addition, the reaction mixture was cooled to 20° C. and a solution of diluted hydrochloric acid to acidic pH was added. The aqueous phase was separated and added dropwise over 1 h to a mixture of water 8.3 g, ethyl acetate 15.3 g and sodium bicarbonate 2.1 g at 60° C. At addition completed and after maintaining the temperature at 60° C. for 1 h, it was checked that the pH was between 4 and 7, the mixture was cooled to 20° C. filtered and dried under vacuum at 50° C. 0.67 g of the compound of formula 1 was obtained with a yield of 75%.

The invention claimed is:

1. A process for the preparation of a compound of formula

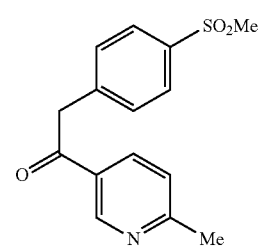

(I)

and salts thereof; which comprises reacting a compound of formula

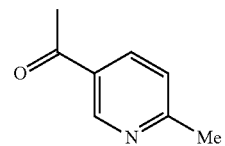

(II)

with a compound of formula

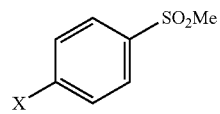

(III)

wherein X is a halogen atom; in the presence of a catalyst, a ligand and a base; wherein said catalyst is a Pd catalyst complex and said ligand is an organophosphoric compound of formula 4,5-Bis-(diphenylphosphino)-9,9-dimethyl-xantene.

2. A process according to claim 1 wherein said Pd catalyst complex is selected from PdCl$_2$, Pd(OAc)$_2$, Pd(dba)$_2$ and Pd$_2$(dba)$_3$.

3. A process according to claim 2 wherein said Pd catalyst complex is selected from Pd(dba)$_2$ and Pd$_2$(dba)$_3$.

4. A process according to claim 3 wherein said Pd catalyst complex is Pd$_2$(dba)$_3$.

5. A process according to claim 1 wherein said base is an alkaline alkoxide.

6. A process according to claim 5 wherein said base is added to the reaction mixture as suspension in 2 to 6 hours.

7. A process according to claim 1 wherein said ligand is in a molar ratio comprised between 1 and 3 with regard to said catalyst complex used.

8. A process according to claim 7 wherein said ligand is in a molar ratio comprised between 1.5 and 2.5 with regard to said catalyst complex used.

9. A process according to claim 1 wherein the loading of said catalyst complex is comprised between 0.05 e 0.50 moles %.

10. A process according to claim 9 wherein the loading of said catalyst complex is 0.10 mole %.

11. A process according to claim 1 wherein said compound of formula I is in hydrochloride salt form.

12. A process according to claim 1 wherein residue X is a bromine atom.

13. A process according to claim 1 wherein said reaction is carried out in the presence of the solvent selected from acetonitrile, diethoxyethane, 2,2-dimethoxypropane, 1,2-dimethoxyethane, dioxane, THF and toluene.

14. A process according to claim 13 of wherein said reaction is carried out in toluene.

15. A process according to claim 1 wherein said reaction is carried out with sodium tert-butoxide in the presence of toluene at reflux temperature.

* * * * *